United States Patent
Jumonji

(10) Patent No.: US 12,080,081 B2
(45) Date of Patent: Sep. 3, 2024

(54) INATTENTIVENESS DETERMINATION DEVICE, INATTENTIVENESS DETERMINATION SYSTEM, INATTENTIVENESS DETERMINATION METHOD, AND STORAGE MEDIUM FOR STORING PROGRAM

(71) Applicant: NEC Corporation, Tokyo (JP)

(72) Inventor: Nana Jumonji, Tokyo (JP)

(73) Assignee: NEC CORPORATION, Tokyo (JP)

( * ) Notice: Subject to any disclaimer, the term of this patent is extended or adjusted under 35 U.S.C. 154(b) by 542 days.

(21) Appl. No.: 17/415,240

(22) PCT Filed: Dec. 24, 2019

(86) PCT No.: PCT/JP2019/050623
§ 371 (c)(1),
(2) Date: Jun. 17, 2021

(87) PCT Pub. No.: WO2020/138088
PCT Pub. Date: Jul. 2, 2020

(65) Prior Publication Data
US 2022/0067411 A1    Mar. 3, 2022

(30) Foreign Application Priority Data
Dec. 27, 2018    (JP) .................... 2018-245790

(51) Int. Cl.
*G06V 20/59*    (2022.01)
(52) U.S. Cl.
CPC ................. *G06V 20/597* (2022.01)

(58) Field of Classification Search
CPC .. G06V 20/597; G06V 40/18; A61B 2503/22; A61B 5/0077; A61B 5/6893;
(Continued)

(56) References Cited

U.S. PATENT DOCUMENTS 10,618,523 B1 *  4/2020  Fields ............. B60W 60/00182
11,562,550 B1 *  1/2023  Asghar .................. G06T 19/20
(Continued)

FOREIGN PATENT DOCUMENTS

| JP | 2009015549 A | 1/2009 |
| JP | 2009157736 A | 7/2009 |
| JP | 2018067198 A | 4/2018 |

OTHER PUBLICATIONS

International Search Report for PCT Application No. PCT/JP2019/050623, mailed on Mar. 17, 2020.

*Primary Examiner* — Mia M Thomas

(57) ABSTRACT

An inattentiveness determination device includes a photographed image acquisition means configured to acquire a photographed image of a driver driving a moving object, a first inattentiveness determination means which detects a gaze direction of the driver according to the photographed image, and determine whether or not the driver is in an inattentiveness state on a basis of a predetermined gaze range based on a moving direction of the moving object and the gaze direction, and a second inattentiveness determination means configured to, if the gaze direction cannot be detected, determine whether or not the driver is in the inattentiveness state on a basis of a face direction of the driver and a predetermined range of the face direction based on the moving direction of the moving object.

12 Claims, 6 Drawing Sheets

(58) Field of Classification Search
CPC . A61B 5/18; G08G 1/166; G08G 3/02; G08B 21/06
See application file for complete search history.

(56) References Cited

U.S. PATENT DOCUMENTS

| | | |
|---|---|---|
| 2009/0009302 A1 | 1/2009 | Matsuoka |
| 2009/0167516 A1 | 7/2009 | Ogawara et al. |
| 2017/0061034 A1* | 3/2017 | Ritchey .................. G09G 5/026 |
| 2018/0111551 A1 | 4/2018 | Suzuki et al. |
| 2019/0135178 A1* | 5/2019 | Shimizu ................... B60Q 9/00 |
| 2019/0161063 A1* | 5/2019 | Awad Alla ........... G06V 20/597 |
| 2019/0236386 A1* | 8/2019 | Yu ......................... G06V 20/597 |
| 2020/0207358 A1* | 7/2020 | Katz ................... G02B 27/0093 |
| 2021/0276568 A1* | 9/2021 | Verbeke ............ B60R 21/01552 |
| 2022/0180109 A1* | 6/2022 | Alpert ........................ G06T 7/70 |
| 2022/0348217 A1* | 11/2022 | Jeong ................... B60W 50/14 |
| 2024/0029453 A1* | 1/2024 | Sano .................... G06V 20/597 |

\* cited by examiner

INATTENTIVENESS DETERMINATION DEVICE, INATTENTIVENESS DETERMINATION SYSTEM, INATTENTIVENESS DETERMINATION METHOD, AND STORAGE MEDIUM FOR STORING PROGRAM

This application is a National Stage Entry of PCT/JP2019/050623 filed on Dec. 24, 2019, which claims priority from Japanese Patent Application 2018-245790 filed on Dec. 27, 2018, the contents of all of which are incorporated herein by reference, in their entirety.

TECHNICAL FIELD

The present invention relates to an inattentiveness determination device, an inattentiveness determination system, an inattentiveness determination method, and a storage medium for storing a program.

BACKGROUND ART

Patent Literature 1 discloses a technology for detecting inattentiveness of a driver who operates a moving object such as a vehicle. In the technology of Patent Literature 1, it is described that once it has been determined based on the direction of a person's face that the person is not looking away, it is determined based on the direction of the person's gaze whether or not the person is looking away.

CITATION LIST

Patent Literature

[Patent Literature 1]
Japanese Unexamined Patent Application, First Publication No. 2009-15549

SUMMARY OF THE INVENTION

Problems to be Solved by the Invention

In the technology of Patent Literature 1, in a case where looking away is determined based on the face direction, even if the gaze direction is not one for which looking away would be determined, looking away is determined.

In order to solve the problems above, the example object of the present invention is to provide an inattentiveness determination device, an inattentiveness determination system, an inattentiveness determination method, and a storage medium for storing a program.

Means for Solving the Problems

According to a first aspect of the present invention, an inattentiveness determination device includes a photographed image acquisition means which acquires a photographed image of a driver driving a moving object, a first inattentiveness determination means which detects a gaze direction of the driver according to the photographed image, and determines whether or not the driver is in an inattentiveness state on a basis of a predetermined gaze range based on a moving direction of the moving object and the gaze direction, and a second inattentiveness determination means which, if the gaze direction cannot be detected, determines whether or not the driver is in the inattentiveness state on a basis of a face direction of the driver and a predetermined range of the face direction based on the moving direction of the moving object.

According to a second aspect of the present invention, in an inattentiveness determination system includes a photographing device and an inattentiveness determination device, wherein the photographing device and the inattentiveness determination device are connected by a communication network. The inattentiveness determination device includes a photographed image acquisition means which acquires a photographed image of a driver driving a moving object, a first inattentiveness determination means which detects a gaze direction of the driver according to the photographed image, and determines whether or not the driver is in an inattentiveness state on a basis of a predetermined gaze range based on a moving direction of the moving object and the gaze direction, and a second inattentiveness determination means which, if the gaze direction cannot be detected, determines whether or not the driver is in the inattentiveness state on a basis of a face direction of the driver and a predetermined range of the face direction based on the moving direction of the moving object.

According to a third aspect of the present invention, an inattentiveness determination method includes acquiring a photographed image of a driver driving a moving object, detecting a gaze direction of the driver according to the photographed image, and determining whether or not the driver is in an inattentiveness state on a basis of a predetermined gaze range based on a moving direction of the moving object and the gaze direction, and determining, if the gaze direction cannot be detected, whether or not the driver is in the inattentiveness state on a basis of a face direction of the driver and a predetermined range of the face direction based on the moving direction of the moving object.

According to a fourth aspect of the present invention, a program stored in a storage medium, in an inattentiveness determination device, executes processes. The processes includes acquiring a photographed image of a driver driving a moving object, detecting a gaze direction of the driver according to the photographed image, and determining whether or not the driver is in an inattentiveness state on a basis of a predetermined gaze range based on a moving direction of the moving object and the gaze direction, and determining, if the gaze direction cannot be detected, whether or not the driver is in the inattentiveness state on a basis of a face direction of the driver and a predetermined range of the face direction based on the moving direction of the moving object.

Advantageous Effects of Invention

According to the present invention, it is possible to more accurately determine whether or not a driver who drives a moving object is in an inattentiveness state.

EXAMPLE EMBODIMENT

Hereinafter, an inattentiveness determination device according to an embodiment of the present invention will be described with reference to the drawings.

Figure 1:
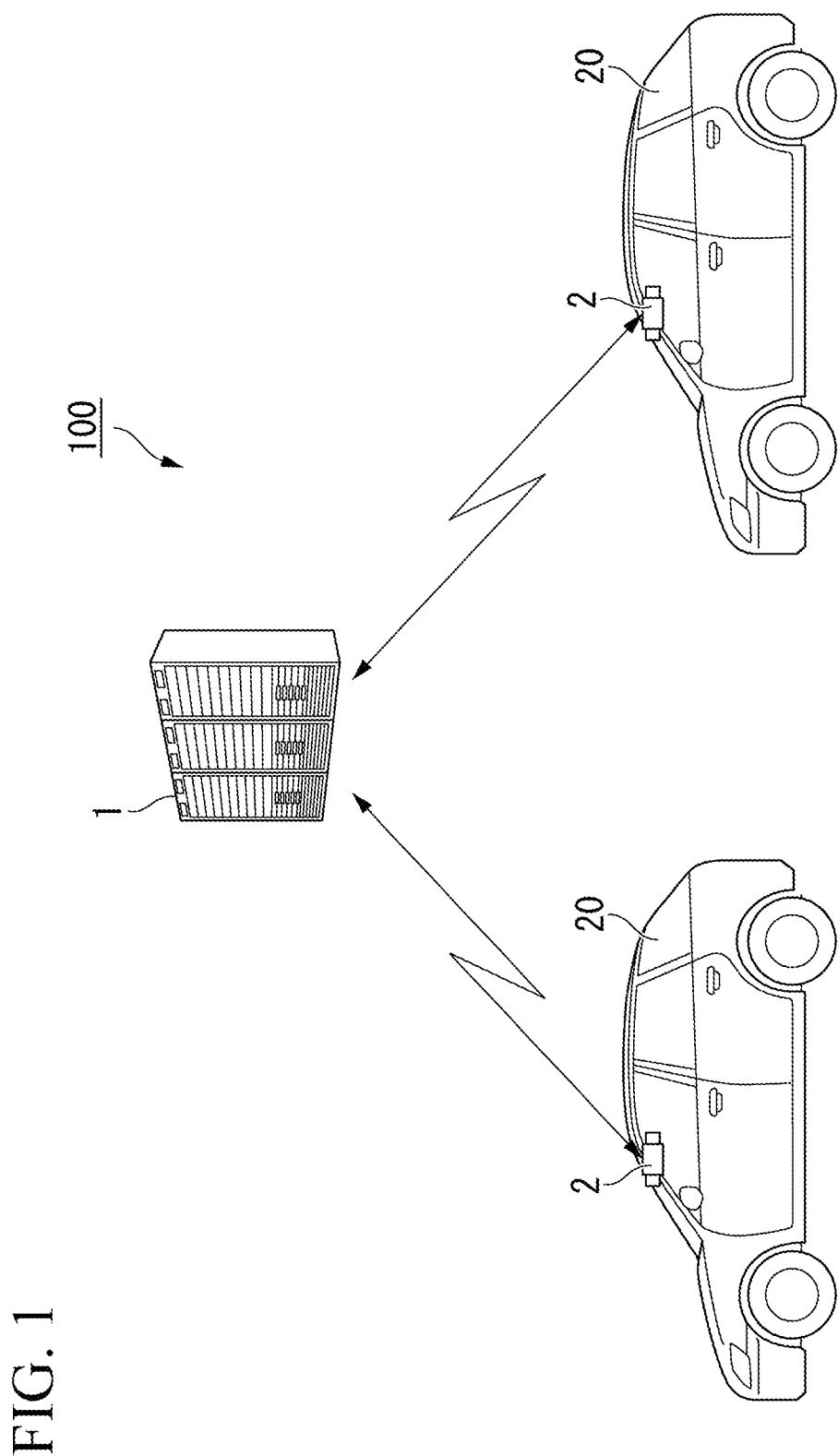
FIG. 1 is a diagram illustrating an inattentiveness determination system according to the present embodiment.

FIG. 1 is a diagram illustrating an inattentiveness determination system according to the present embodiment.

As shown in FIG. 1, an inattentiveness determination system 100 is configured to include an inattentiveness determination device 1 and a drive recorder 2 as one aspect of a driving condition sensing device. The drive recorder 2, as an example, may be installed near a windshield of a vehicle 20, which is a moving object. The inattentiveness determination device 1 and the drive recorder 2 are connected via a wireless communication network or a wired communication network. The inattentiveness determination device 1 is connected in communication with, for example, the drive recorders 2 installed in each of a plurality of vehicles 20.

Figure 2:
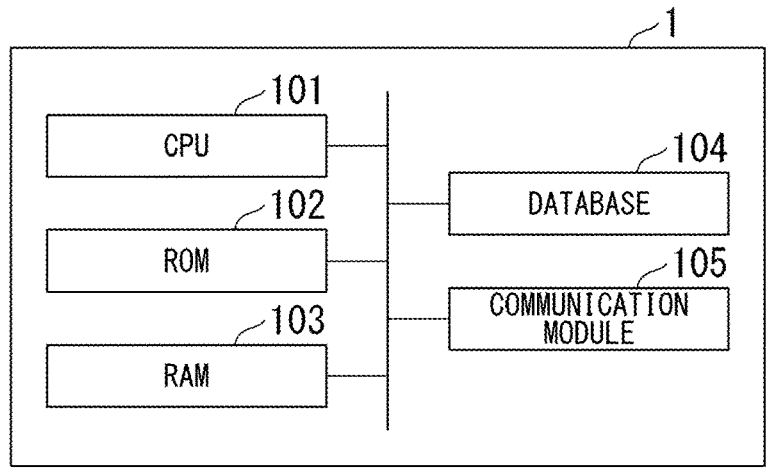
FIG. 2 is a hardware configuration diagram of an inattentiveness determination device according to the present embodiment.

FIG. 2 is a hardware configuration diagram of an inattentiveness determination device.

The inattentiveness determination device 1, as shown in the figure, is a computer equipped with hardware such as a central processing unit (CPU) 101, a read only memory (ROM) 102, a random access memory (RAM) 103, a database 104, and a communication module 105.

Figure 3:
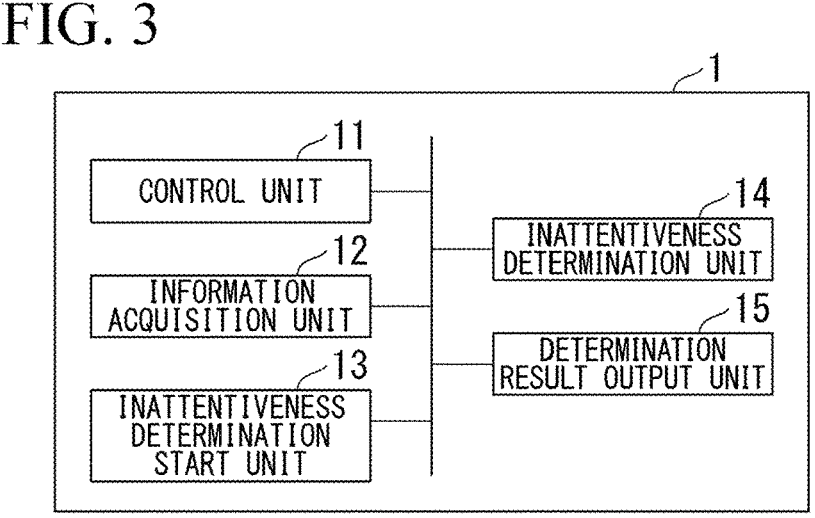
FIG. 3 is a functional block diagram of an inattentiveness determination device according to the present embodiment.

FIG. 3 is a functional block diagram of an inattentiveness determination device.

The inattentiveness determination device 1 operates when power is turned on, and executes an inattentiveness determination program stored in advance. As a result, the inattentiveness determination device 1 includes at least a control unit 11, an information acquisition unit 12, an inattentiveness determination start unit 13, an inattentiveness determination unit 14, and a determination result output unit 15.

The control unit 11 controls other functional units.

The information acquisition unit 12 acquires information transmitted from the drive recorder 2 such as a photographed image, vehicle information, weather information, acceleration information, and the like.

The inattentiveness determination start unit 13 determines whether to start inattentiveness determination.

The inattentiveness determination unit 14 determines whether or not a driver is in an inattentiveness state.

The determination result output unit 15 outputs an inattentiveness determination result.

Figure 4:
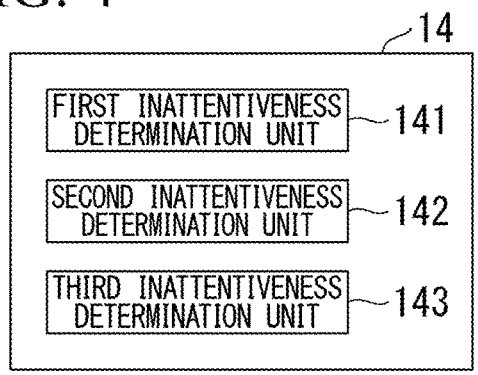
FIG. 4 is a functional block diagram illustrating the details of an inattentiveness determination part according to the present embodiment.

FIG. 4 is a functional block diagram illustrating the details of an inattentiveness determination unit.

As shown in FIG. 4, the inattentiveness determination unit 14 has functions of a first inattentiveness determination unit 141, a second inattentiveness determination unit 142, and a third inattentiveness determination unit 143.

In particular, the first inattentiveness determination unit 141 detects the gaze direction of a driver based on the photographed image, and determines whether or not the driver is in an inattentiveness state according to the gaze direction and a predetermined gaze range based on the moving direction of the moving object. In this process, the first inattentiveness determination unit 141 may measure the time when the gaze direction is not included in the predetermined gaze range, and may determine the inattentiveness state when a ratio per unit time of the measured time is equal to or greater than a predetermined ratio.

Further, if the gaze direction cannot be detected, the second inattentiveness determination unit 142 determines whether or not the driver is in the inattentiveness state according to a predetermined range of the face direction based on the moving direction of the moving object and the driver's face direction. In this process, the second inattentiveness determination unit 142 measures the time when the face direction is not included in the predetermined range of the face direction, and determines the inattentiveness state when the ratio per unit time of the measured time is equal to or greater than the predetermined ratio.

Further, if the driver's face direction cannot be detected in a case where the gaze direction cannot be detected, the third inattentiveness determination unit 143 determines whether or not the driver's face can be detected according to the photographed image. If the third inattentiveness determination unit 143 cannot detect the driver's face, it is determined as in the inattentiveness state. In this process, the third inattentiveness determination unit 143 detects a time when the driver's face cannot be detected, and determines the inattentiveness state when the ratio per unit time of the detected time is equal to or greater than the predetermined ratio.

Figure 5:
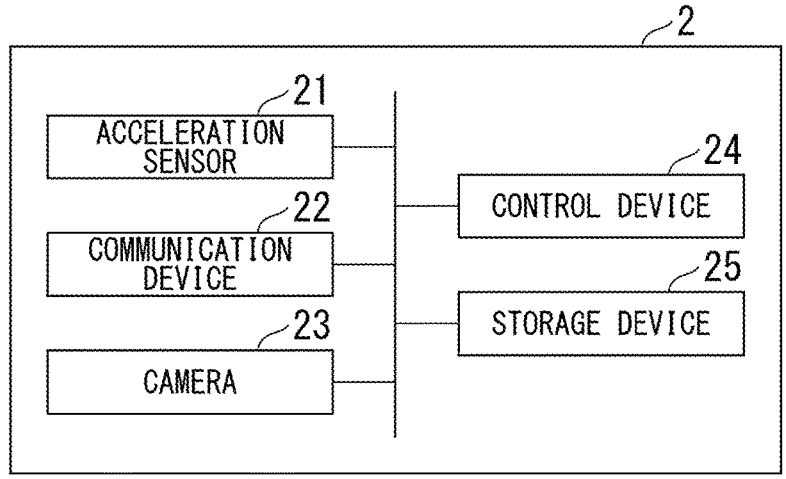
FIG. 5 is a diagram illustrating a hardware configuration of a drive recorder according to the present embodiment.

FIG. 5 is a diagram showing a hardware configuration of a drive recorder.

The drive recorder 2 is configured to include an acceleration sensor 21, a communication device 22, a camera 23 (a photographing device), a control device 24, a storage device 25, and the like. The acceleration sensor 21 detects acceleration of the vehicle. The communication device 22 is connected in communication with the inattentiveness determination device 1. The camera 23 photographs the outside or the inside of the vehicle to generate at least one of a moving image and a still image.

The control device 24 controls each function of the drive recorder 2. The storage device 25 stores either a moving image or a still image, the acceleration sensed by the acceleration sensor 21, other information acquired from the outside of the drive recorder 2, and the like. The drive recorder 2 is connected in communication with the inattentiveness determination device 1 via a base station or the like. In addition, the control device 24 of the drive recorder 2 is a computer equipped with a CPU, a ROM, a RAM, and the like.

Figure 6:
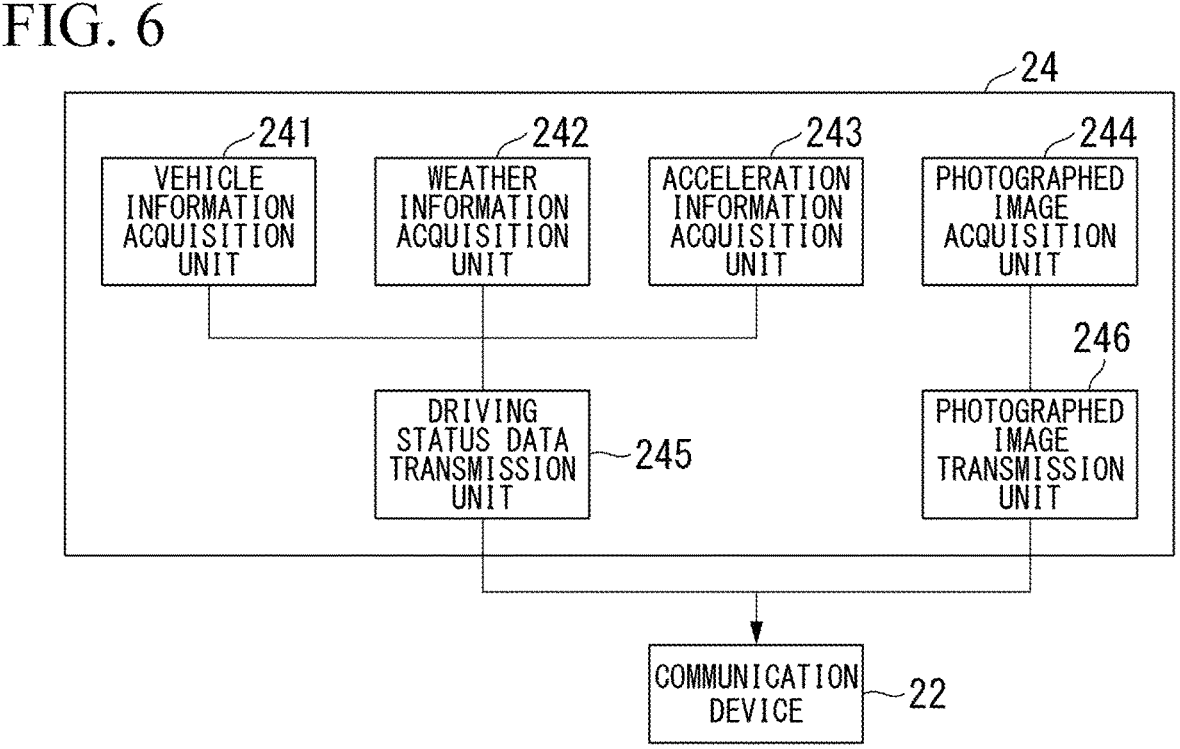
FIG. 6 is a functional block diagram of a control device of a drive recorder according to the present embodiment.

FIG. 6 is a functional block diagram of the control device 24 provided in the drive recorder 2.

The control device 24 executes the control program when the drive recorder 2 is activated. As a result, the control device 24 includes various units such as a vehicle information acquisition unit 241, a weather information acquisition unit 242, an acceleration information acquisition unit 243, a photographed image acquisition unit 244, a driving status data transmission unit 245, and a photographed image transmission unit 246.

Figure 7:
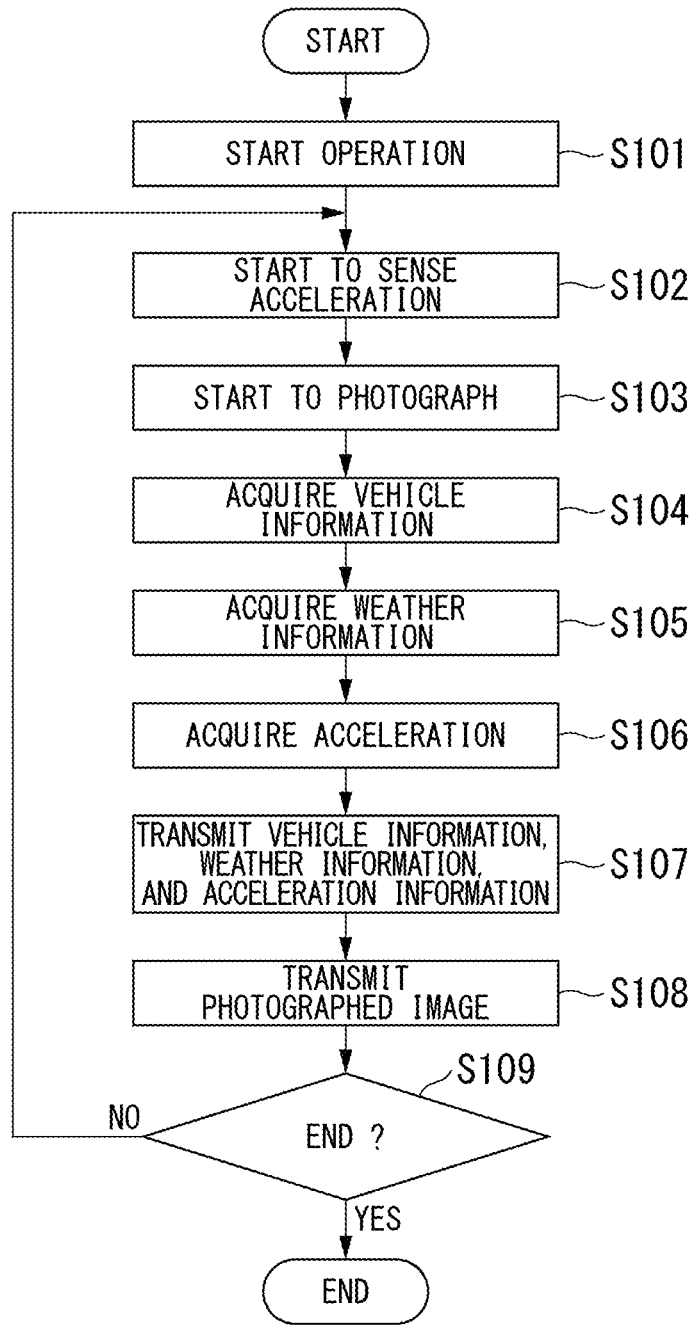
FIG. 7 is a diagram illustrating a process flow of a drive recorder according to the present embodiment.

FIG. 7 is a diagram illustrating a process flow of the drive recorder 2.

The process flow of the inattentiveness determination system 100 will be explained in order.

First, a transmission process of the driving status information in the drive recorder 2 will be described.

When the electric system of the vehicle 20 is activated, the drive recorder 2 starts to operate (step S101). The acceleration sensor 21 of the drive recorder 2 starts to sense the acceleration of the vehicle after the drive recorder 2 is activated (step S102). Further, the camera 23 starts to photograph inside and outside the vehicle (step S103). The camera 23 may include a vehicle inner lens and a vehicle outer lens. The camera 23 photographs the inside of the vehicle using the vehicle inner lens, and photographs an object in the direction of the driver's face inside the vehicle. The camera 23 uses the vehicle outer lens to photograph an object in the moving direction outside the vehicle.

The vehicle information acquisition unit 241 of the control device 24 acquires vehicle information while the drive recorder 2 is operating (step S104). The vehicle information acquired by the vehicle information acquisition unit 241 is a vehicle speed, a steering wheel angle, a signal light direction, and the like detected by each sensor provided in the vehicle. In the present embodiment, the vehicle information includes at least the vehicle speed and the signal light direction. The vehicle information may further include information other than the steering wheel angle and the signal light direction.

Further, the weather information acquisition unit 242 acquires the weather information (step S105). The weather information may be obtained from a server device provided by the Japan Meteorological Agency or a weather information providing company. Alternatively, the weather information may be information obtained from a sensor (wiper motion detector or raindrop detector) provided in the vehicle. The control device 24 may determine that it is raining when the wiper is operating or when the raindrop detector detects raindrops.

The acceleration information acquisition unit 243 acquires the acceleration from the acceleration sensor 21 at a predetermined time interval (step S106). The control device 24 acquires the vehicle information, the weather information, and the acceleration at a predetermined interval. Although, in the present embodiment, it is described that the control device 24 acquires the weather information and the acceleration, the acquisition of the weather information and the acceleration may not be necessary.

Further, during the operation of the drive recorder 2, the photographed image acquisition unit 244 of the control device 24 acquires a photographed image (at least one of a moving image and a still image) from the camera 23. The photographed image includes at least information on a range of the driver's face. The photographed image acquisition unit 244 outputs the photographed image to the photographed image transmission unit 246.

The driving status data transmission unit 245 instructs the communication device 22 to transmit the vehicle information, the weather information, and the acceleration information to the inattentiveness determination device 1 at a predetermined interval. The communication device 22 transmits the vehicle information, the weather information, and the acceleration information to the inattentiveness determination device 1 (step S107). Further, if the weather information and the acceleration are not acquired in the control device 24, such information may not be transmitted to the inattentiveness determination device 1.

The photographed image transmission unit 246 instructs the communication device 22 to transmit the photographed image to the inattentiveness determination device 1. The communication device 22 transmits the photographed image to the inattentiveness determination device 1 (step S108). The control device 24 determines whether or not the process has ended (step S109), and repeats the process from step S102 until it is determined that the process has ended. Further, an ID of the drive recorder 2, an ID of the driver, and the sensing time are assigned to the vehicle information, the weather information, the acceleration information, and the photographed image.

Figure 8:
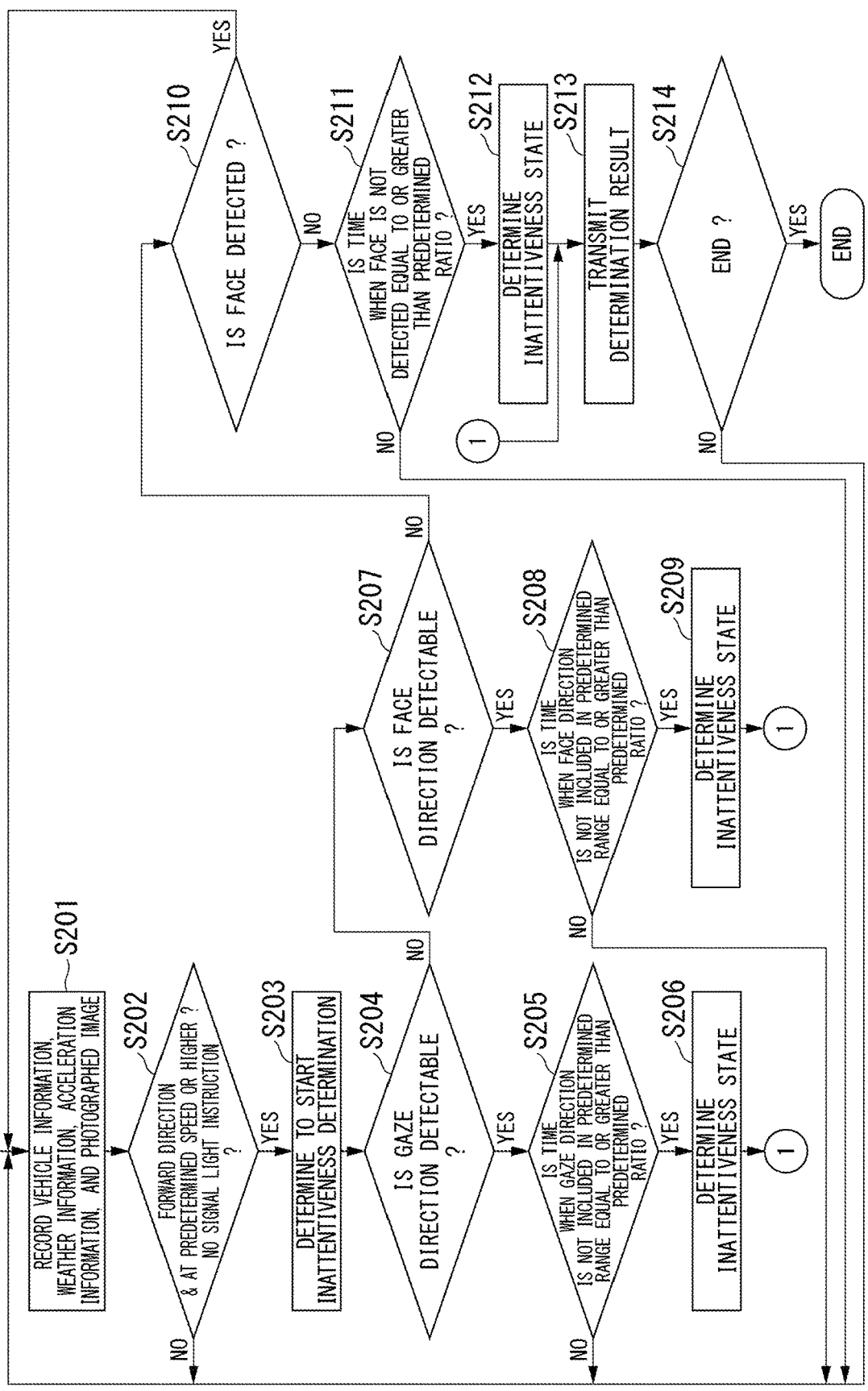
FIG. 8 is a diagram illustrating a process flow of an inattentiveness determination device according to the present embodiment.

FIG. 8 is a diagram illustrating a process flow of the inattentiveness determination device 1.

In the inattentiveness determination device 1, the information acquisition unit 12 associates a set of corresponding vehicle information, weather information, acceleration information, and a photographed image with each ID, according to the ID of the drive recorder 2 and the ID of the driver, and then, sequentially records the associated set in the database 104 (step S201). Then, the control unit 11 instructs the inattentiveness determination start unit 13 and the inattentiveness determination unit 14 to perform the inattentiveness determination process.

The inattentiveness determination start unit 13 identifies a certain drive recorder 2 and acquires the sensing time, the vehicle information, the weather information, the acceleration information, and the photographed image recorded in association with the ID of the identified drive recorder 2.

The inattentiveness determination unit 14 determines whether the vehicle speed included in the vehicle information indicates a predetermined speed or higher as the speed in the forward direction (forward) and whether or not the signal light direction does not designate a direction instruction (step S202). The predetermined speed may be a value such as about 20 km/h as an example. If the vehicle speed indicates a predetermined speed or higher in the forward direction and the signal light instruction is not designated (YES in step S202), the inattentiveness determination unit 14 decides to start the inattentiveness determination (step S203).

The inattentiveness determination start unit 13 may decide to start the inattentiveness determination by using other information or by using the information and other added information. For example, the inattentiveness determination unit 14 may determine whether or not the acceleration is 0 or more, and may decide to start the inattentiveness determination if the acceleration is 0 or more. Further, the inattentiveness determination unit 14 may decide whether or not to start the inattentiveness determination depending on whether or not the steering wheel angle is in a predetermined range. The predetermined range of the steering wheel angle may be, for example, about 10 degrees to the left or right based on the forward direction. Further, the inattentiveness determination unit 14 may decide to start the inattentiveness determination if the weather information indicates rain.

The inattentiveness determination unit 14 may decide whether or not to start the inattentiveness determination according to the photographed image outside the vehicle. For example, it may decide to start the inattentiveness determination if an object is captured in the forward direction of the photographed image or if a curve of a lane is captured in the photographed image. The inattentiveness determination unit 14 may decide whether or not to start the inattentiveness determination according to accident information on the road on which the vehicle 20 travels and information on a nearby event. In a case where the drive recorder 2 detects dangerous vehicle events (situations with a possibility of developing into an accident), the inattentiveness determination unit 14 may decide to start the inattentiveness determination when the drive recorder 2 has detected a dangerous event.

If it is decided to start the inattentiveness determination, the inattentiveness determination unit 14 instructs start. The inattentiveness determination unit 14 repeats the determination process of whether or not to start the inattentiveness determination at predetermined intervals.

The inattentiveness determination unit 14 receives the photographed image already acquired by the information acquisition unit 12 from the information acquisition unit 12 according to the ID of the drive recorder 2 of the current object to be processed. If the inattentiveness determination unit 14 decides to start the inattentiveness determination, among the photographed images received from the drive recorder 2 at a predetermined interval, the photographed image taken inside the vehicle is sequentially read.

If the inattentiveness determination unit 14 reads the photographed image of the inside of the vehicle, the first inattentiveness determination unit 141 determines whether or not the direction of the driver's gaze can be detected using the newly acquired photographed image (step S204). The first inattentiveness determination unit 141 performs a calculation of the gaze direction using a known technique.

If the gaze direction can be detected as a result of the gaze direction calculation process, the first inattentiveness determination unit 141 measures the time when the gaze direction is not included in a first predetermined range based on the forward direction. The first predetermined range may be a range such as about 10 degrees to the left and right based on the forward direction. When a speed is low, a driver is more likely to see a wide area. Therefore, the first inattentiveness determination unit 141 may widen the width of the first predetermined range based on the forward direction to about 20 degrees to the left and right.

The first inattentiveness determination unit 141 determines whether or not the time when the gaze direction is not included in the first predetermined range based on the forward direction is equal to or greater than a first predetermined ratio per unit time. (Step S205). If the ratio per unit time of the time when the gaze direction is not included in the first predetermined range based on the forward direction is equal to or greater than the first predetermined ratio (YES in step S205), the first inattentiveness determination unit 141 determines that the driver is in an inattentiveness state (step S206). If the first inattentiveness determination unit 141 determines that the ratio per unit time of the time when the gaze direction is not included in the first predetermined range based on the forward direction is not equal to or greater than the first predetermined ratio (NO in step S205), the control unit 11 performs control such that the process is repeated from step S201.

The time when the gaze direction is not included in the first predetermined range based on the forward direction may be a continuous time within a predetermined time or a total time of an intermittent time within the predetermined time.

If it is determined in step S204 that the direction of the driver's gaze cannot be detected (NO in step S204), the first inattentiveness determination unit 141 instructs the second inattentiveness determination unit 142 to start processing. The second inattentiveness determination unit 142 determines whether or not the direction of the driver's face can be detected using the photographed image (step S207). The second inattentiveness determination unit 142 performs the calculation of the face direction using a known technique.

If the face direction can be detected as a result of the face direction calculation process (YES in step S207), the second inattentiveness determination unit 142 measures the time when the face direction is not included in a second predetermined range based on the forward direction. The second predetermined range may be a range of about 10 degrees to the left and right based on the forward direction. When a speed is low, the driver is more likely to see a wide area. Therefore, the second inattentiveness determination unit 142 may widen the width of the second predetermined range based on the forward direction to about 20 degrees to the left and right. The second predetermined range may be a range different from the first predetermined range.

The second inattentiveness determination unit 142 determines whether or not the ratio per unit time of the time when the face direction is not included in the second predetermined range based on the forward direction is equal to or greater than the second predetermined ratio (step S208). If the ratio per unit time of the time when the face direction is not included in the second predetermined range based on the forward direction is equal to or greater than the second predetermined ratio (step YES in S208), the second inattentiveness determination unit 142 determines that the driver is in an inattentiveness state (step S209). If the second inattentiveness determination unit 142 determines that the ratio per unit time of the time when the face direction is not included in the second predetermined range based on the forward direction is not equal to or greater than the second predetermined ratio (NO in step S208), the control unit 11 performs control such that the process is repeated from step S201.

The time when the face direction is not included in the second predetermined range based on the forward direction may be a continuous time within a predetermined time, or a total time of an intermittent time within the predetermined time. The first predetermined ratio and the second predetermined ratio may be different values from each other.

If it is determined in step S207 that the direction of the driver's face cannot be detected (NO in step S207), the second inattentiveness determination unit 142 instructs the third inattentiveness determination unit 143 to start processing. The third inattentiveness determination unit 143 determines whether or not the driver's face is detected using the photographed image (step S210). The third inattentiveness determination unit 143 determines whether or not a face is detected by using a known technique.

If it is determined that the face is not detected as a result of determining whether or not the face is detected (NO in step S210), the third inattentiveness determination unit 143 measures the time when the face is not detected. The third inattentiveness determination unit 143 determines whether or not the ratio per unit time of the time when the face is not detected is equal to or greater than a third predetermined ratio (step S211). If the ratio per unit time of the time when the face is not detected is equal to or greater than the third predetermined ratio (YES in step S211), the third inattentiveness determination unit 143 determines that the driver is in an inattentiveness state (step S212). If the third inattentiveness determination unit 143 determines that the ratio per unit time of the time when the face is not detected is not equal to or greater than the third predetermined ratio (NO in step S211), the control unit 11 performs control such that the process is repeated from step S201.

The time when the face is not detected may be a continuous time within a predetermined time or a total time of an intermittent time within the predetermined time. The third predetermined ratio may be a value different from the first predetermined ratio and the second predetermined ratio.

If it is determined that the inattentiveness has occurred (steps S206, S209, S212), the inattentiveness determination unit 14 instructs the determination result output unit 15 to output the inattentiveness determination result. The determination result output unit 15 acquires the ID of the drive recorder 2 that has determined the occurrence of inattentiveness. The determination result output unit 15 acquires the network address of the drive recorder 2 as the transmission destination from the database 104 according to the ID of the drive recorder 2. The network address of the transmission destination may be recorded in the database 104 in advance. The determination result output unit 15 transmits information indicating the detection of inattentiveness to the drive recorder 2 of the transmission destination (step S213). The determination result output unit 15 may record in the database 104 the information indicating the detection of inattentiveness in association with the ID of the drive recorder 2 or the ID of the driver.

The inattentiveness determination unit 14 determines whether or not to end the process (step S214). If it determines not to end the process (NO in step S214), the inattentiveness determination device 1 then repeats the same process at a predetermined interval using the information received from the drive recorder 2 and the like.

The drive recorder 2 receives the information on inattentiveness detection from the inattentiveness determination device 1. If the drive recorder 2 receives the information on the inattentiveness detection, the drive recorder 2 performs a process of notifying the driver of the inattentiveness detection, such as sending out an alarm sound. This allows the driver to recognize the inattentive driving.

In the above process, the inattentiveness determination device 1 connected to a communication network as a cloud server performs the inattentiveness determination. However, the drive recorder 2 may independently perform the above-described processing of the inattentiveness determination. That is, the drive recorder 2 may operate as the inattentiveness determination device 1. In this case, the drive recorder 2 may perform the same processes as the above-described information acquisition unit 12, the inattentiveness determination start unit 13, the inattentiveness determination unit 14, and the determination result output unit 15.

Alternatively, an on-board device connected to the drive recorder 2 and mounted inside the vehicle 20 may be provided with the processes of the information acquisition unit 12, the inattentiveness determination start unit 13, the inattentiveness determination unit 14, and the determination result output unit 15. In this case, the on-board device operates as the inattentiveness determination device 1. In this case, the on-board device performs the same processes as the information acquisition unit 12, the inattentiveness determination start unit 13, the inattentiveness determination unit 14, and the determination result output unit 15.

According to the above-described processing, it is possible to more accurately determine whether or not a driver who drives a moving object is in an inattentiveness state. That is, according to the above-described processing, the inattentiveness determination device 1 first detects the direction of the driver's gaze, and determines whether or not the driver is in the inattentiveness state on a basis of the gaze direction and a predetermined gaze range based on the forward direction of the vehicle 20. After that, if the gaze direction cannot be detected, the inattentiveness determination device 1 determines whether or not the driver is in the inattentiveness state based on the direction of the driver's face.

In this way, the inattentiveness determination device 1 determines the inattentiveness state based on the gaze direction before determining the inattentiveness state based on the face direction. Therefore, even if the face direction is not in a predetermined range, if the driver is not inattentive because the gaze direction is toward the moving direction, the inattentiveness determination device 1 that does not misrecognize this as the inattentiveness state can be provided.

Further, according to the above processing, an inattentiveness detection alert is not issued for a slight deviation of the face direction or the gaze direction, but the inattentiveness detection alert is issued if the face direction or the gaze direction deviates by a predetermined ratio or more in a predetermined period. As a result, it is possible to reduce the output of unnecessary inattentiveness alerts to the driver.

Further, according to the above-described inattentiveness determination device 1, it is possible to avoid determining inattentiveness in a situation where the gaze direction is likely to deviate from a front in a case of low-speed driving lower than a predetermined speed. As a result, it is possible to reduce the output of unnecessary inattentiveness detection alerts to the driver.

For example, the inattentiveness determination device 1 performs a process of expanding the range based on the forward direction when it is determined that there is a possibility of inattentiveness determination in response to a decrease in the speed of the vehicle. At this time, the first predetermined range and the second predetermined range may be expanded, or one of the predetermined ranges may be increased. The degree of increase may differ between the first predetermined range and the second predetermined range. As a result, it is possible to determine the inattentiveness according to the appropriate range of the face direction and the gaze direction in response to the speed.

Further, in the process of determining whether the ratio per unit time of the time when the gaze is included in the predetermined range based on the forward direction is equal to or greater than the predetermined ratio, the inattentiveness determination device 1 may increase the value of the predetermined ratio as the speed decreases. At this time, all of the first predetermined ratio, the second predetermined ratio, and the third predetermined ratio may be increased, or only some of the predetermined ratios may be increased. The degree of increase may differ between the first predetermined ratio, the second predetermined ratio, and the third predetermined ratio. As a result, it is possible to determine the inattentiveness on the basis of the appropriate range of the face direction and the gaze direction in response to the speed.

In the above-described embodiment, it is described that the moving object is the vehicle 20, but the inattentiveness determination device 1 may determine the inattentiveness of a driver of another moving object such as a ship or an aircraft.

Figure 9:
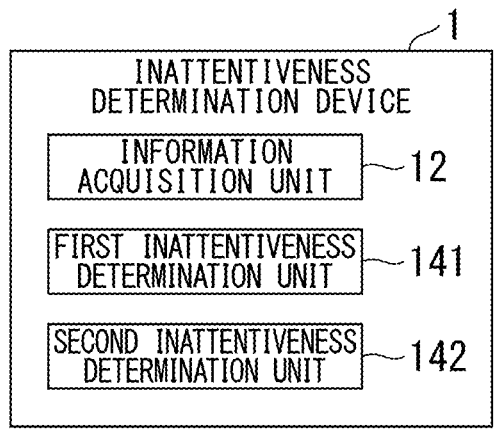
FIG. 9 is a diagram illustrating a minimum configuration of an inattentiveness determination device according to the present embodiment.

FIG. 9 is a diagram illustrating the minimum configuration of the inattentiveness determination device 1.

Figure 10:
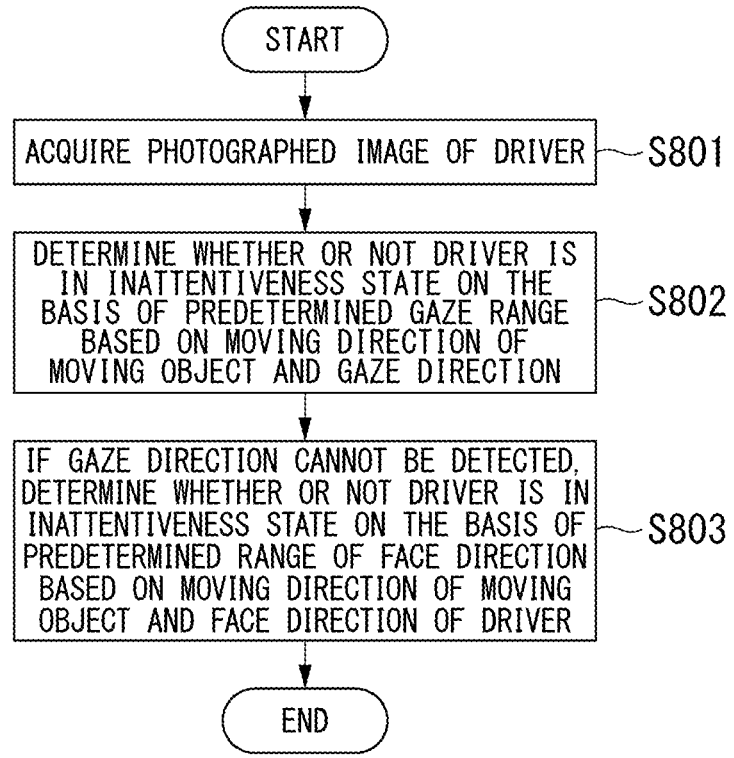
FIG. 10 is a diagram illustrating a process flow of an inattentiveness determination device with a minimum configuration according to the present embodiment.

FIG. 10 is a diagram illustrating a process flow of the inattentiveness determination device 1 having the minimum configuration.

The inattentiveness determination device 1 may include at least the information acquisition unit 12 (photographed image acquisition unit), the first inattentiveness determination unit 141, and the second inattentiveness determination unit 142.

The information acquisition unit 12 acquires a photographed image of the driver who drives the moving object (step S801).

The first inattentiveness determination unit 141 detects the direction of the driver's gaze based on the photographed image, and determines whether or not the driver is in the inattentiveness state on a basis of a predetermined gaze range based on the moving direction of the moving object and the gaze direction (step S802).

If the gaze direction cannot be detected, the second inattentiveness determination unit 142 determines whether or not the driver is in the inattentiveness state on a basis of a predetermined range of the face direction based on the moving direction of the moving object and the direction of the driver's face. (Step S803).

The above-described inattentiveness determination device 1 and drive recorder 2 have a computer system inside. The process of each operation described above is stored in a computer-readable recording medium in the form of a program, and the process is performed by the computer reading and executing this program. Here, the computer-readable recording medium is a magnetic disk, a magnetic-optical disc, a CD-ROM, a DVD-ROM, a semiconductor memory, or the like. Further, this computer program may be distributed to a computer via a communication line, and the computer receiving the distribution may execute the program.

Further, the above program may be one for implementing some of the above-described functions. Additionally, a so-called patch file (patch program) may be used, which can implement the above-described functions in combination with a program already recorded in the computer system.

Priority is claimed on Japanese Patent Application No. 2018-245790, filed Dec. 27, 2018, the content of which is incorporated herein by reference.

INDUSTRIAL APPLICABILITY

According to the present invention, it is possible to more accurately determine whether or not a driver who drives a moving object is in an inattentiveness state.

REFERENCE SIGNS LIST

1 Inattentiveness determination device
2 Drive recorder
11 Control unit
12 Information acquisition unit
13 Inattentiveness determination start unit
14 Inattentiveness determination unit
15 Determination result output unit
21 Acceleration sensor
23 Camera
24 Control device
141 First inattentiveness determination unit
142 Second inattentiveness determination unit
143 Third inattentiveness determination unit
241 Vehicle information acquisition unit
242 Weather information acquisition unit
243 Acceleration information acquisition unit
244 Photographed image acquisition unit
245 Driving status data transmission unit
246 Photographed image transmission unit

What is claimed is:

1. An inattentiveness determination device, comprising:
at least one memory storing instructions; and
at least one processor configured to execute the instructions to:
acquire a photographed image of a driver driving a moving object;
detect a gaze direction of the driver according to the photographed image, and determine whether or not the driver is in an inattentiveness state on a basis of a predetermined gaze range based on a moving direction of the moving object and the gaze direction; and
determine, if the gaze direction cannot be detected, whether or not the driver is in the inattentiveness state on a basis of a face direction of the driver and a predetermined range of the face direction based on the moving direction of the moving object, by measuring a time when the face direction is not in the predetermined range of the face direction and determining that the driver is in the inattentiveness state if a ratio per unit time of the measured time is equal to or greater than a second predetermined ratio.

2. The inattentiveness determination device according to claim 1,
wherein the at least one processor is configured to execute the instructions to determine whether or not the driver is in the inattentiveness state on the basis of the predetermined gaze range based on the moving direction of the moving object and the gaze direction by measuring a time when the gaze direction is not in the predetermined gaze range and determining that the driver is in the inattentiveness state if a ratio per unit time of the measured time is equal to or greater than a first predetermined ratio.

3. The inattentiveness determination device according to claim 1,
wherein the at least one processor is further configured to execute the instructions to:
determine, in a case where the gaze direction and the face direction cannot be detected, whether or not a face of the driver can be detected on a basis of the photographed image and determine that the driver is in the inattentiveness state if the face of the driver cannot be detected.

4. The inattentiveness determination device according to claim 3,
wherein the at least one processor is configured to execute the instructions to determine that the driver is in the inattentiveness state if the face of the driver cannot be detected by detecting a time when the face of the driver cannot be detected, and determining that the driver is in the inattentiveness state when a ratio per unit time of the detected time is equal to or greater than a third predetermined ratio.

5. An inattentiveness determination method performed by a processor and comprising:
acquiring a photographed image of a driver driving a moving object;
detecting a gaze direction of the driver according to the photographed image, and determining whether or not the driver is in an inattentiveness state on a basis of a predetermined gaze range based on a moving direction of the moving object and the gaze direction; and
determining, if the gaze direction cannot be detected, whether or not the driver is in the inattentiveness state on a basis of a face direction of the driver and a predetermined range of the face direction based on the moving direction of the moving object, by measuring a time when the face direction is not in the predetermined range of the face direction and determining that the driver is in the inattentiveness state if a ratio per unit time of the measured time is equal to or greater than a second predetermined ratio.

6. The inattentiveness determination method according to claim 5, wherein
determining whether or not the driver is in the inattentiveness state on the basis of the predetermined gaze range based on the moving direction of the moving object and the gaze direction comprises measuring a time when the gaze direction is not in the predetermined gaze range is measured and determining that the driver is in the inattentiveness state if a ratio per unit time of the measured time is equal to or greater than a first predetermined ratio.

7. The inattentiveness determination method according to claim 5, further comprising
determining, in a case where the gaze direction and the face direction cannot be detected, whether or not a face of the driver can be detected on a basis of the photographed image and determining that the driver is in the inattentiveness state if the face of the driver cannot be detected.

8. The inattentiveness determination method according to claim 7, wherein
determining that the driver is in the inattentiveness state if the face of the driver cannot be detected comprises detecting a time when the face of the driver cannot be detected, and determining that the driver is in the inattentiveness state when a ratio per unit time of the detected time is equal to or greater than a third predetermined ratio.

9. A non-transitory computer-readable storage medium storing a program executable by an inattentiveness determination device to perform processes comprising:
acquiring a photographed image of a driver driving a moving object;
detecting a gaze direction of the driver according to the photographed image, and determining whether or not the driver is in an inattentiveness state on a basis of a predetermined gaze range based on a moving direction of the moving object and the gaze direction; and
determining, if the gaze direction cannot be detected, whether or not the driver is in the inattentiveness state on a basis of a face direction of the driver and a predetermined range of the face direction based on the moving direction of the moving object, by measuring a time when the face direction is not in the predetermined range of the face direction and determining that the driver is in the inattentiveness state if a ratio per unit time of the measured time is equal to or greater than a second predetermined ratio.

10. The non-transitory computer-readable storage medium according to claim 8, wherein
determining whether or not the driver is in the inattentiveness state on the basis of the predetermined gaze range based on the moving direction of the moving object and the gaze direction comprises measuring a time when the gaze direction is not in the predetermined gaze range is measured and determining that the driver is in the inattentiveness state if a ratio per unit time of the measured time is equal to or greater than a first predetermined ratio.

11. The non-transitory computer-readable storage medium according to claim 8, wherein the processes further comprise
determining, in a case where the gaze direction and the face direction cannot be detected, whether or not a face of the driver can be detected on a basis of the photographed image and determining that the driver is in the inattentiveness state if the face of the driver cannot be detected.

12. The non-transitory computer-readable storage medium according to claim 11, wherein
determining that the driver is in the inattentiveness state if the face of the driver cannot be detected comprises detecting a time when the face of the driver cannot be detected, and determining that the driver is in the inattentiveness state when a ratio per unit time of the detected time is equal to or greater than a third predetermined ratio.

* * * * *